US007251335B1

(12) United States Patent
Chen

(10) Patent No.: US 7,251,335 B1
(45) Date of Patent: Jul. 31, 2007

(54) SELF CONTAINED MP3 PLAYER AND EARPHONES

(76) Inventor: Jinsuan Chen, 2nd. Fl., NO. 8 & 10, Lane 337, Yung Ho Road, Chung Ho City, Taipei (TW)

( * ) Notice: Subject to any disclaimer, the term of this patent is extended or adjusted under 35 U.S.C. 154(b) by 0 days.

(21) Appl. No.: 11/405,398

(22) Filed: Apr. 18, 2006

(51) Int. Cl.
*A61F 11/06* (2006.01)
*H04R 1/10* (2006.01)
*H04R 5/02* (2006.01)

(52) U.S. Cl. ........................ 381/71.6; 381/74; 381/384

(58) Field of Classification Search ................ 381/370, 381/371, 374, 384; 455/575.2
See application file for complete search history.

(56) References Cited

U.S. PATENT DOCUMENTS

| | | | | |
|---|---|---|---|---|
| 5,604,813 | A * | 2/1997 | Evans et al. | 381/71.6 |
| 6,728,585 | B2 * | 4/2004 | Neoh | 700/94 |
| 6,829,365 | B1 * | 12/2004 | Kim | 381/370 |
| 6,965,681 | B2 * | 11/2005 | Almqvist | 381/371 |
| 6,993,140 | B1 * | 1/2006 | Chen | 381/71.6 |
| 2003/0012396 | A1 * | 1/2003 | Smith | 381/381 |
| 2003/0073460 | A1 * | 4/2003 | van Pelt et al. | 455/556 |
| 2005/0069146 | A1 * | 3/2005 | Bum | 381/74 |
| 2005/0201569 | A1 * | 9/2005 | Kuraoka et al. | 381/74 |
| 2006/0019729 | A1 * | 1/2006 | Harris | 455/575.6 |
| 2006/0088171 | A1 * | 4/2006 | Yeh | 381/74 |
| 2006/0185062 | A1 * | 8/2006 | Peng et al. | 2/209.13 |

* cited by examiner

*Primary Examiner*—Xu Mei

(57) ABSTRACT

A headset containing 2 earphones is described. The headset includes an anti-noise circuit, a radio system circuit, and a sound collection circuit for providing an anti-noise capability. One of the earphones defines a cavity having an external input terminal therein. An output terminal of a conventional MP3 player is coupled to the external input terminal when the player is disposed in the cavity. The output terminal is coupled to the radio system circuit so that music played by the MP3 player can be transmitted to the earphones. A keeper is provided to retain the MP3 player in the cavity.

7 Claims, 8 Drawing Sheets

SELF CONTAINED MP3 PLAYER AND EARPHONES

FIELD OF THE INVENTION

This invention relates to a noise cancellation headset or earphones, and in particular to such a headset which contains a MP3 player.

BACKGROUND OF THE INVENTION

As is well known, a number of MP3 players have been developed which are quite small in size. In particular, MP3 players are available now which are about the size of a business card or a package of chewing gum. Such players are loaded with music for example from a desktop computer so that the user can play whatever music is desired. Because of the size, the MP3 players do not include a speaker. Accordingly, the user must wear a headset in order to receive a digital signal from the MP3 player which is coupled to the headset by an audio cable to play music through the headset.

Music from an MP3 player is coupled by an audio lead to the user through either earplugs, or a conventional headset which carries microphones covering the ears.

It is also known to provide a headset containing a memory card to generate the music played through the microphones. Such a device is shown for example in U.S. Pat. No. 6,829,365.

It is also known to provide headsets which operate to cancel external noise so that the wearer can concentrate on a desired source of music. In such a device, the unwanted exterior noise is detected, and a canceling signal of an opposite phase generated. A second microphone then detects the desired sounds and transmits them to the user through the earphones. Such a device is described in my U.S. Pat. No. 6,993,140. The disclosure of that patent is hereby incorporated by reference. In that patent application, three different functions were combined in a single system. The system contained an anti-noise circuit, a radio-receiving circuit, and a sound collection circuit. The device then would eliminate external noise or background noise, and receive a radio broadcast from an external audio source. The device further included a sound collection system for the anti-noise circuit. The anti-noise circuit system included a microphone to receive the external or background noise and a circuit for generating a compensating signal of an opposite wave length to cancel the background noise. The radio circuit could include a microphone for receiving the radio sound, or more likely, from a sound generating device hardwired to said circuit for producing music or the like.

SUMMARY OF THE INVENTION

The instant invention includes a headset which contains the three circuits above-described, the anti-noise circuit, the radio-receiving circuit, and the sound collection circuit. These circuits function as above-described and described in my prior patent application. The improvement herein lies in a recess formed in one of the earphones of the headset and an external audio input terminal mounted within said recess, coupled to said radio circuit. The terminal is an elongated pin. A conventional MP3 player then can be mounted in the recess engaging the terminal so that music from said MP3 player can be broadcast through the headset to the wearer. In this way, any conventional MP3 player can be removably mounted in the headset when desired. The invention then eliminates the need for an audio cable connecting the source of the music with the headset as in conventional devices.

As an additional embodiment of the invention, the headset can have only an anti-noise circuit, or none of the three internal circuits identified above.

Accordingly it is an object of this invention to provide an audio headset with a circuit to eliminate background noise and having a recess for removably mounting a conventional MP3 player therein which is internally coupled to a radio circuit.

It is another object of this invention to provide a conventional MP3 player and headset therefore which includes anti-noise features and wherein the MP3 player can be removed as desired.

It is yet another object of this invention to provide a headset for an MP3 player, which does not utilize an audio cable connecting between the headset and the MP3 player.

These and other object will become readily apparent with reference to the drawings and following description wherein:

DETAILED DESCRIPTION OF THE INVENTION

Figure 1:
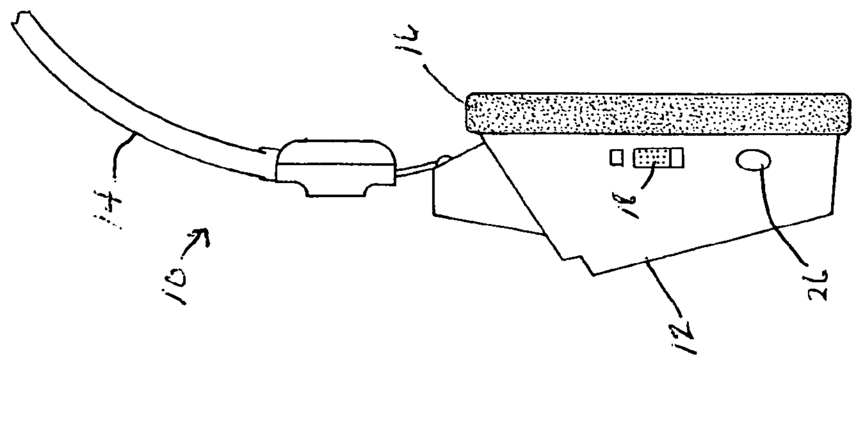
FIG. 1 is a side view of an embodiment of this invention.
Figure 2:
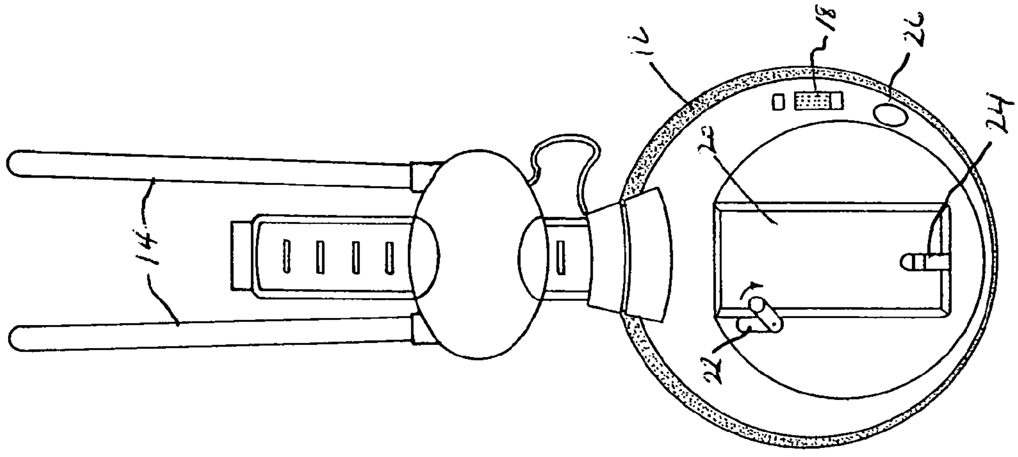
FIG. 2 is a front view of the embodiment of FIG. 1.
Figure 3:
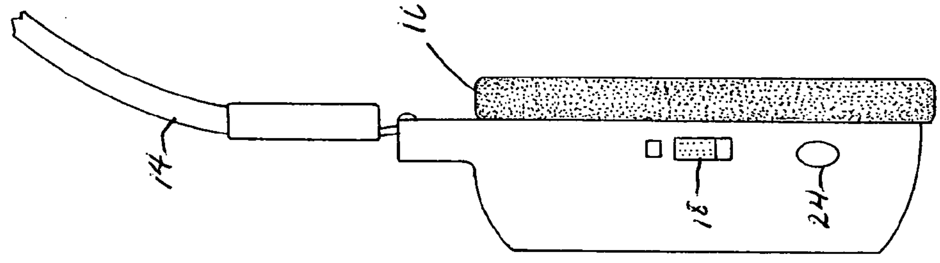
FIG. 3 is a side view of another embodiment of this invention.
Figure 4:
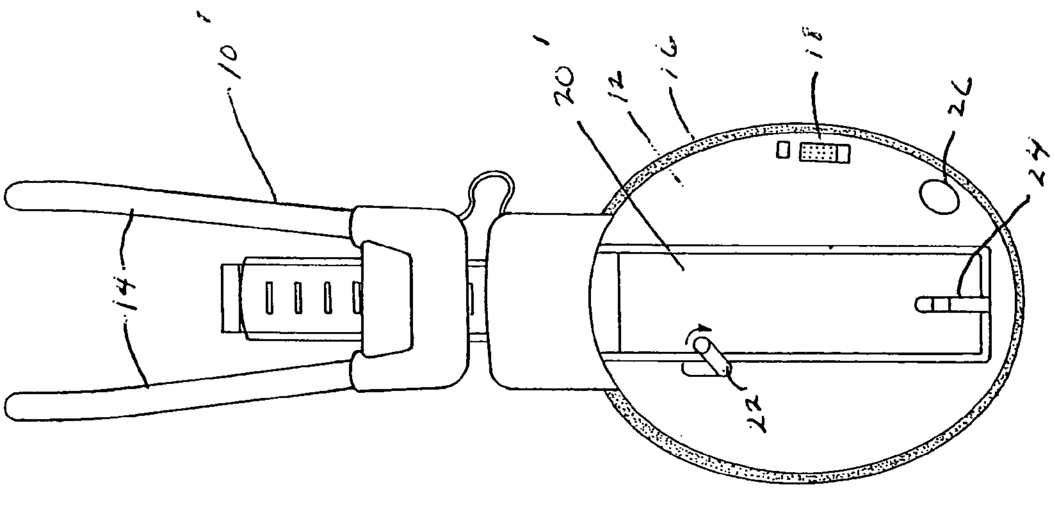
FIG. 4 is a front view of the embodiment of FIG. 3.

With attention to the drawing and to FIGS. 1–4 in particular, a headset 10 which consists of proposed earpieces 12 is shown. Only a single of said earpieces 12 is shown, but it should be understood that an opposite earpiece is disposed at the end of cord 14. Earpiece 12 has a conventional pad 16 and provides an on/off switch 18 to control an anti-noise circuit. The earpiece 12 defines a cavity 20 with a keeper lever 22 and an external audio input terminal 24. A second external input terminal 26 is also provided. Terminal 26 can be utilized if it is desired to use an audio cable lead to connect the headset 10 with an external source of music or the like. However, in the preferred embodiment of this invention a conventional MP3 player is mounted by keeper 22 in cavity 20 and receives terminal 24 in an output terminal (not shown) of said MP3 player. Conventional MP3 players (not shown) such as the Apple I-Pod Shuffle can be utilized in cavity 20. The embodiment of FIGS. 3 and 4 differs from the embodiment of FIGS. 1 and 2 in the size of the cavity 20'. As shown in the drawings the cavity 20' is elongated as compared to the cavity 20 so that it can receive a differently shaped MP3 player. The headset 10 or 10' functions in a conventional fashion except for the above-described improvements.

Accordingly there is a second earpiece (not shown) which is coupled to the line 14 so that sounds generated by the MP3 player disposed in cavity 20 or cavity 20' is transferred to both of the earpieces.

Figure 5:
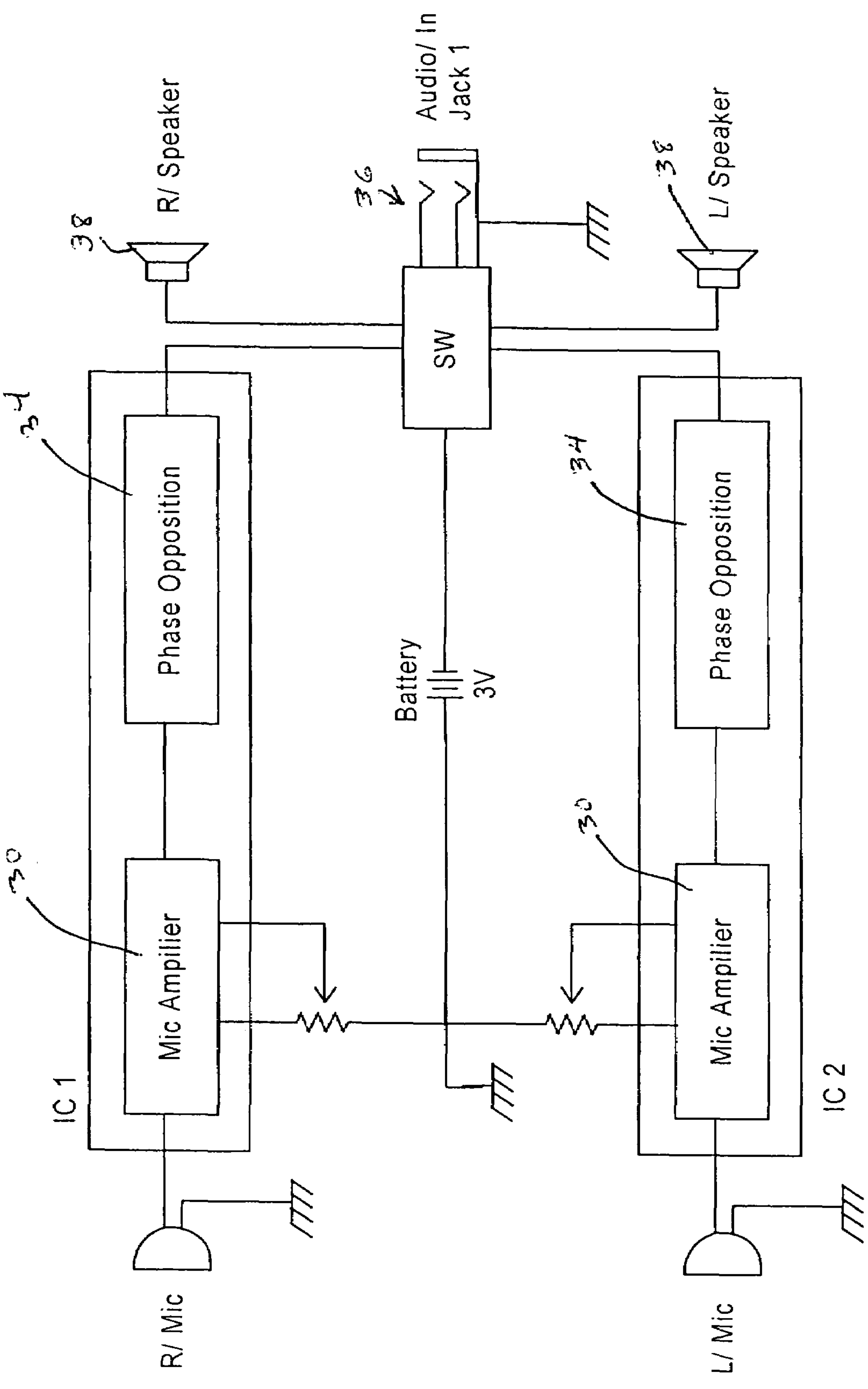
FIG. 5 is a schematic of the anti-noise circuit for the device of this invention.

With attention to the schematic of FIG. 5, twin microphones 30 receive the background noise and an opposite phase signal is generated at 34. The phase signal generated, then cancels the background noise picked up in microphones 30. The audio input desired then is provided at the audio jack 36.

Speakers 38 correspond then to the headset earpieces. In this way a background noise can be eliminated, and the desired audio input can be heard through the earpieces 38.

It will be obvious to those skilled in the art that if it is desired merely to protect the ears from the background noise the audio input can be eliminated. However, this invention resides in the improvement above noted wherein a conventional MP3 player can be mounted in the headset rather than be carried separately with an audio cable connecting between the MP3 player and the headset. The need for an audio lead cable then is eliminated.

Figure 6:
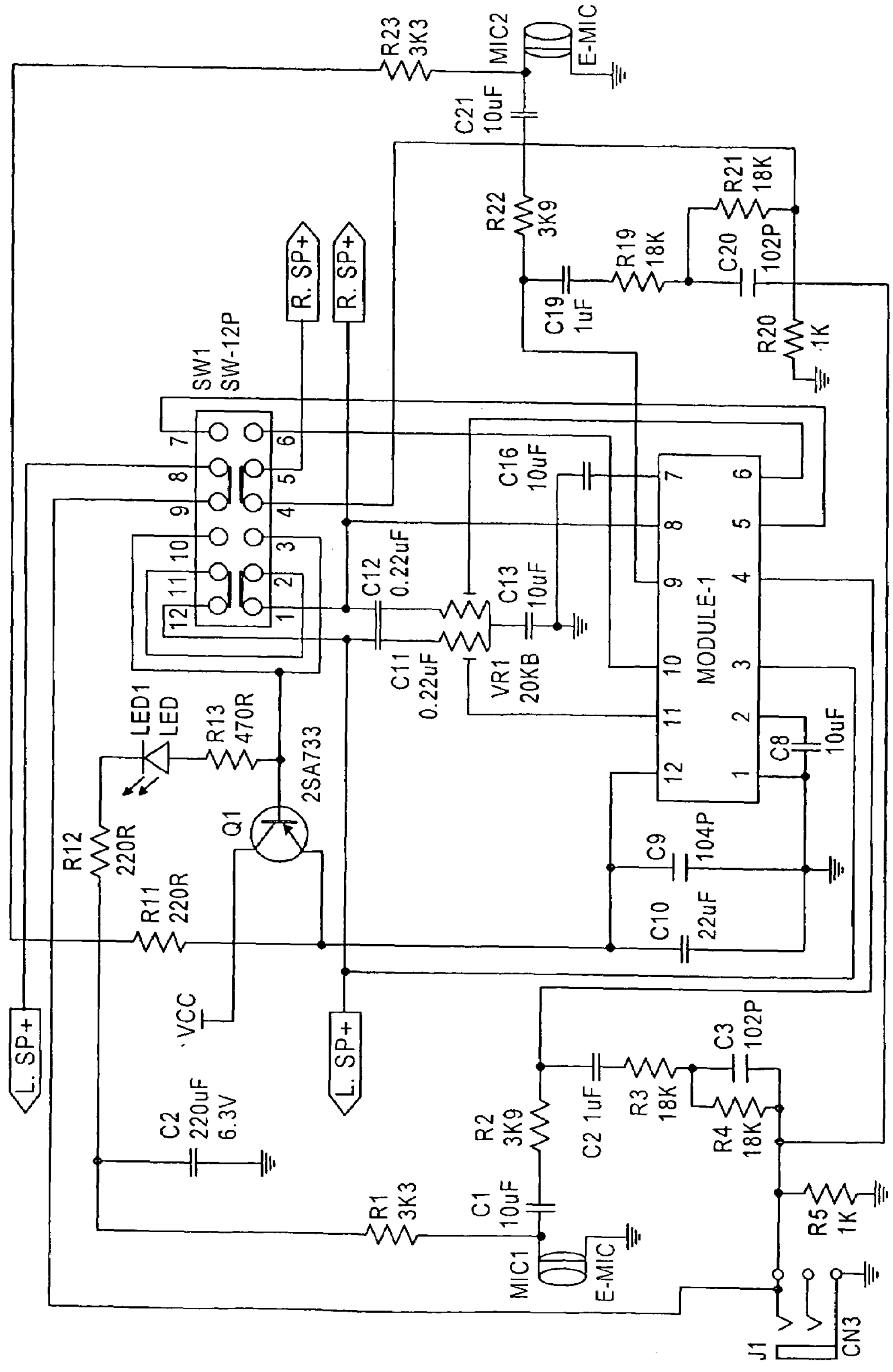
FIG. 6 is a wiring diagram for the embodiment of FIG. 5.

FIG. 6 is a conventional circuit diagram for the schematic of FIG. 5.

As will be obvious to those skilled in the art a number of conventional MP3 players could be utilized with the headset of this invention. Representative of such MP3 players are manufactured for example by Apple and marketed as the Shuffle or the Nano or other well known devices. MP3 players are also manufactured by a number of companies such as Sony. The I-Pod Shuffle is about the size of a business card, and will easily fit in the cavity shown as reference number 20 or 20'. Since it weighs less than 1 ounce it will not be uncomfortable for the wearer of the headset. The MP3 player, itself, is not part of this invention which is directed to the headset described above.

Figure 7:
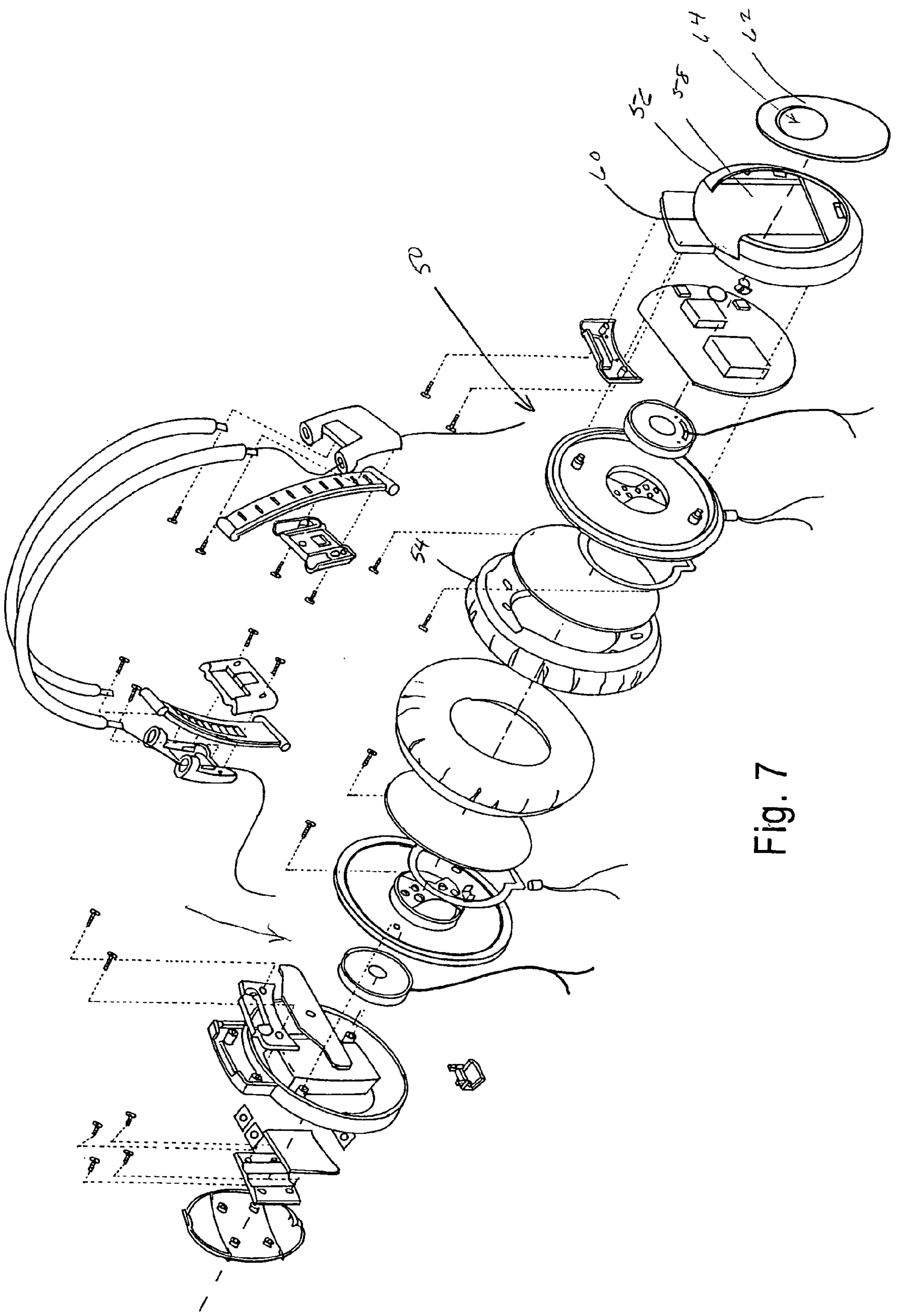
FIG. 7 is an exploded view of the embodiment of FIGS. 1 and 2.
Figure 8:
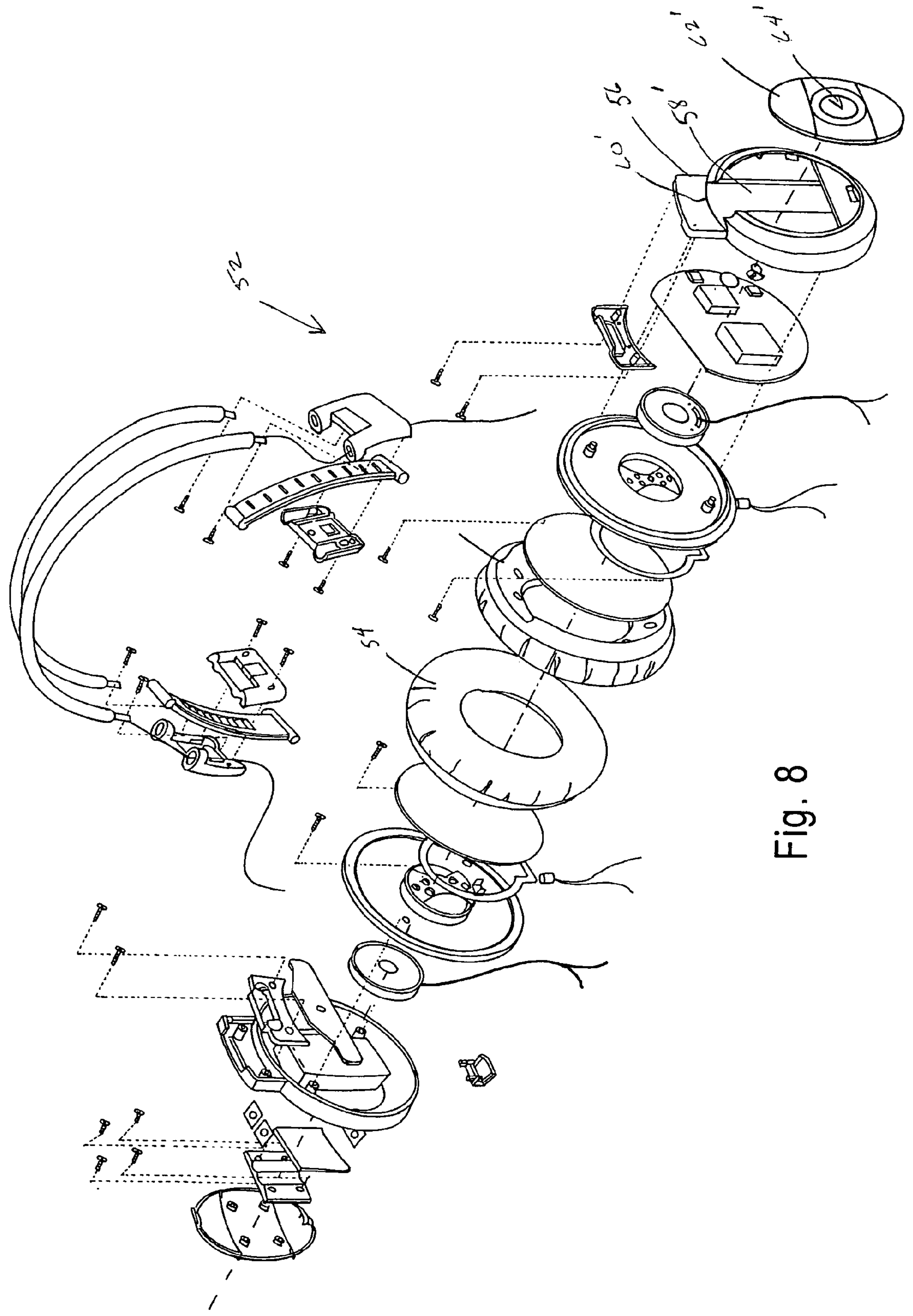
FIG. 8 is an exploded view of the embodiment of FIGS. 3 and 4.

FIGS. 7 and 8 show additional embodiments 50 and 52. In these embodiments headphone 54 carries member 56 with a recess 58 in FIGS. 7 and 58' in FIG. 8. Recesses 58 and 58' are intended to receive a MP3 player (not shown). The player is intended to be inserted into member 56 through the gap 60 and 60'. Recess 58 is then covered by cover plate 62 or 62' which serves to protect the MP3 player which would be mounted in slot 58 or 58'. An opening in plate 62 or 62', 64 or 64' is also provided, but the opening is optional.

Accordingly the headset 50 or 52 can be modified by covering an exposed MP3 player mounted in one of said headphones 54 by providing a cover plate 62 or 62' covering the recess 58 or 58' which mounts the MP3 player. The structure of the headphones 50 or 52 is the same as that described for FIGS. 1-6 with the difference being the presence of the cover plate 62 or 62'.

Figure 9:
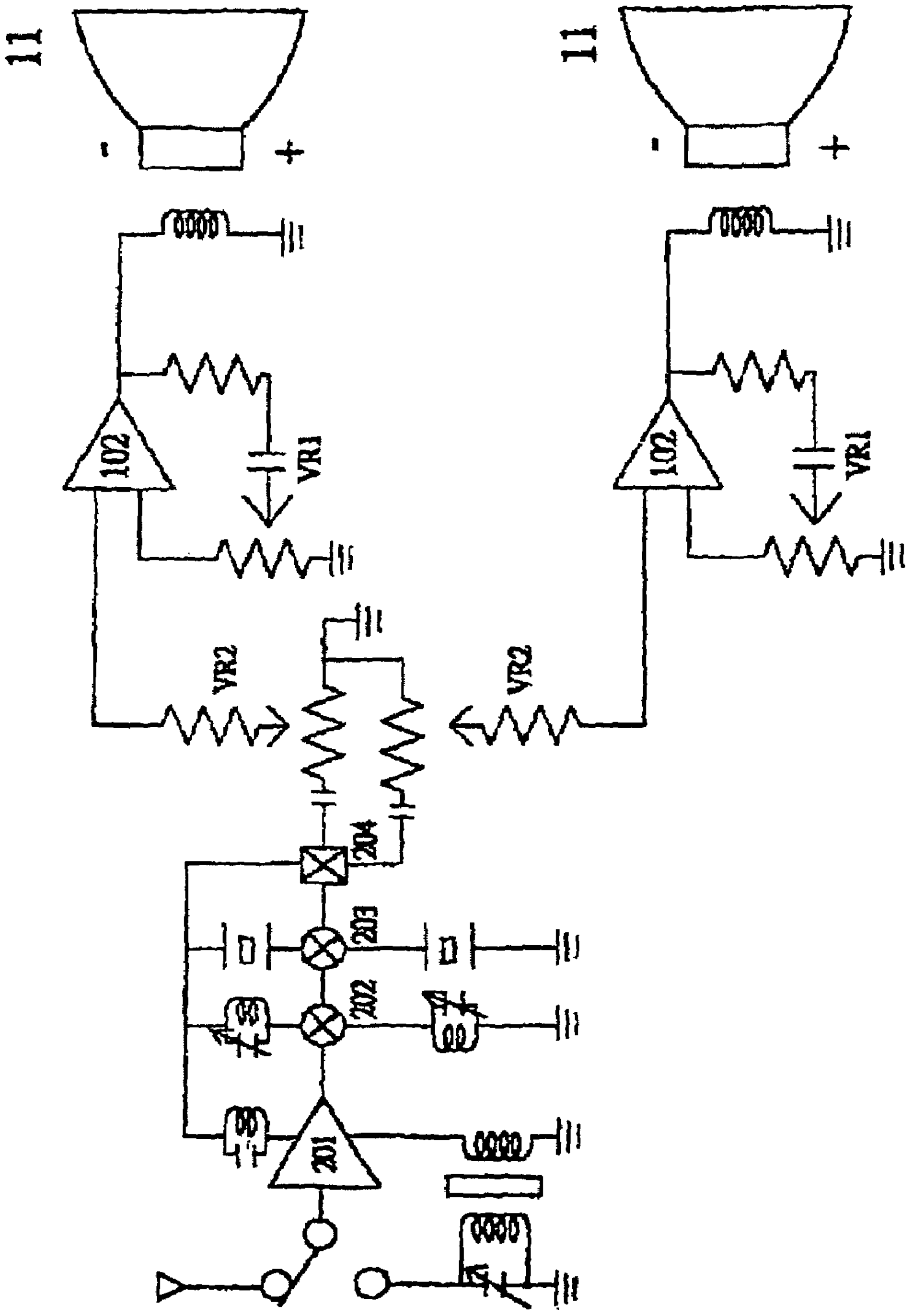
FIG. 9 is a circuit diagram of the radio receiving circuit of this invention.
Figure 10:
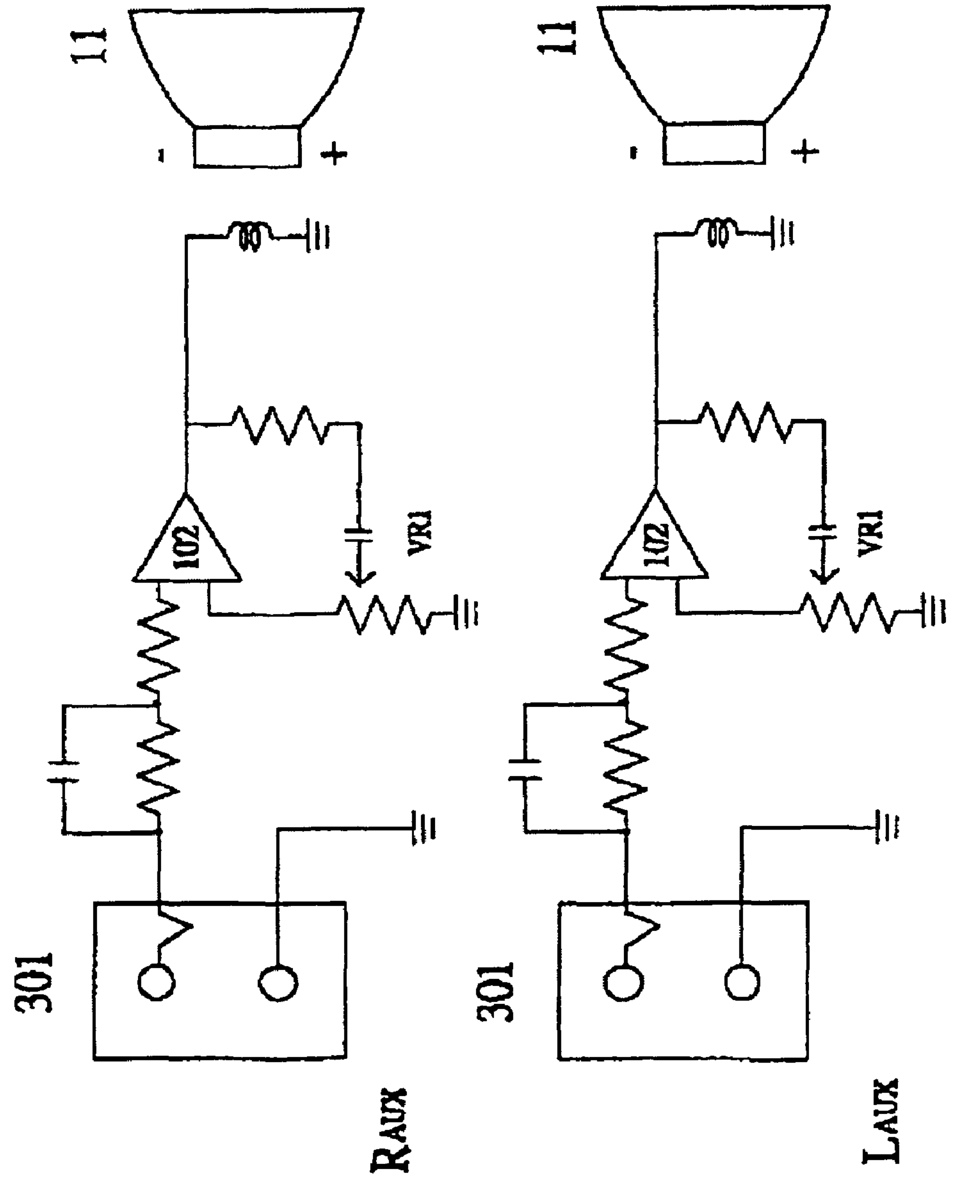
FIG. 10 is a circuit diagram of the sound-collection circuit of this invention.
Figure 11:
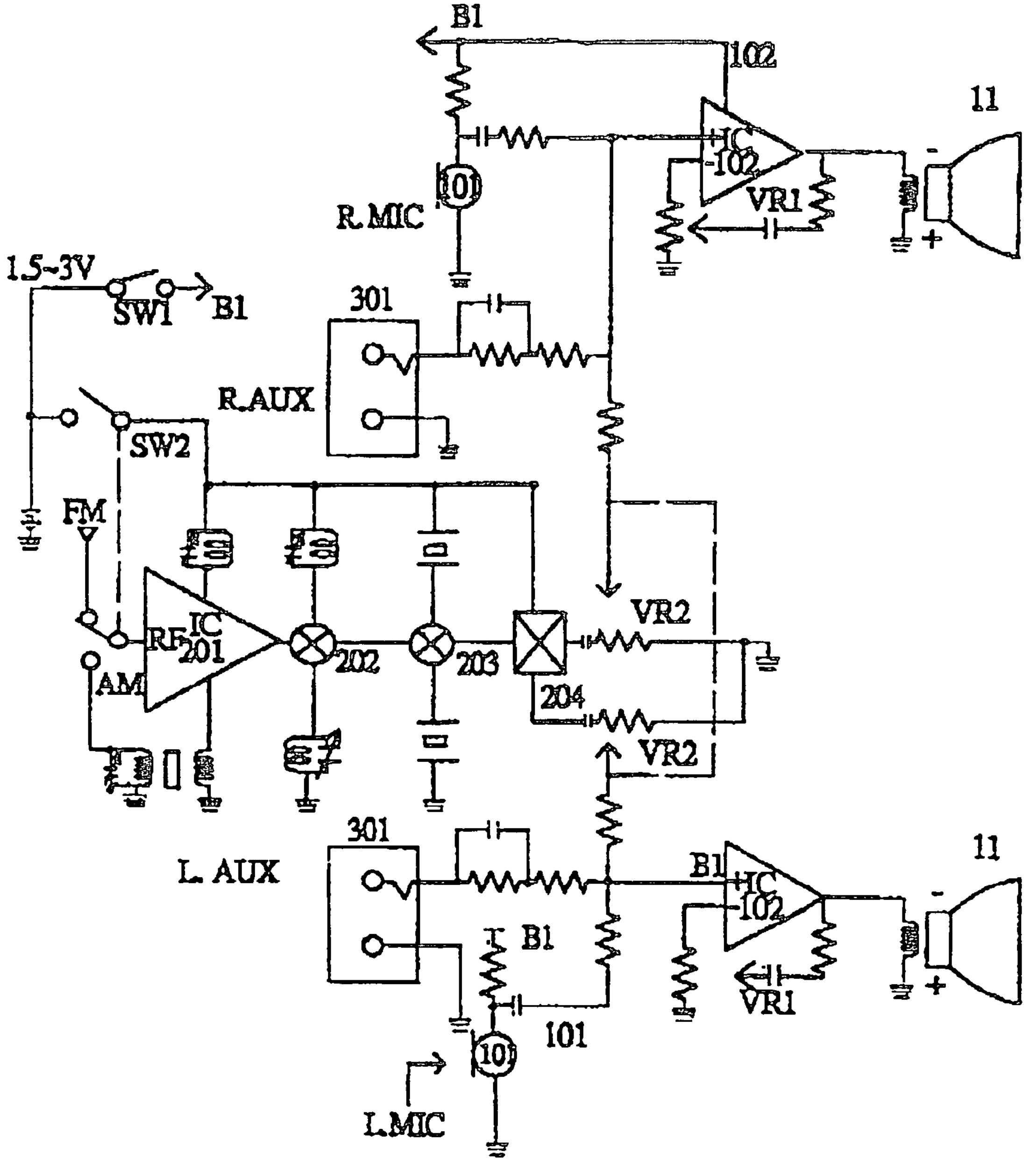
FIG. 11 is a circuit diagram of a synthesis circuit combining the components of FIGS. 4, 9 and 10.

FIGS. 9 and 10 are a radio receiving circuit, and a sound collection circuit which with the anti-noise circuit could be embodied in the headphone of this invention. These Figures correspond to drawings in U.S. Pat. No. 6,993,140 for a 3-In-1 Anti-Noise Radio Sound Collection Device. That patent was incorporated by reference herein. FIG. 11 is a circuit diagram of the synthesis circuit combining these three components. This drawing is also similar to one in U.S. Pat. No. 6,993,140.

It will be readily seen by one of ordinary skill in the art that the present invention fulfills all of the objects set forth above. After reading the foregoing specifications, one of ordinary skill will be able to effect various changes, substitutions or equivalents and various other aspects of the invention as broadly disclosed herein. It is therefore intended that the protection granted hereon be limited only by the definition contained in the appended claims and equivalents thereof.

What is claimed is:

1. A headphone structure having right and left ear cover speakers, a headband interconnecting the speakers and first, second, and third circuit systems therein;

said first circuit system being an anti-noise circuit compromising a microphone for detecting noise, phase detection U circuits coupled to said microphone and to each speaker and means for emitting a sound wave of opposite phase to said noise, coupled to said speakers;

said second circuit system being a radio circuit system comprising an AM/FM receiver, a U circuit IC, a down converter circuit, a detect circuit, and a demodulator circuit;

said third circuit system being a sound collection circuit system comprising an external source audio input terminal, said second circuit system demodulator circuit and said third circuit system audio input terminal being coupled to said phase detecting U circuits in said first circuit system and to said speakers;

said headphone system further comprising a cavity formed in the external surface of one of said ear cover speakers, said cavity containing an external input terminal and said cavity being dimensioned sufficiently to receive a MP3 player therein which player is coupled to said external input terminal;

said external input terminal disposed in said cavity being coupled to said radio circuit;

and a keeper means disposed adjacent said cavity for retaining said MP3 player therein.

2. The structure of claim 1 wherein said keeper means is a pivotally mounted lever.

3. The structure of claim 1 further comprising a protective cover plate dimensioned to cover said cavity whereby when said MP3 player is mounted therein coupled to said external input terminal, said cover plate will protect said MP3 player.

4. The structure of claim 3 wherein said cover plate defines an opening there through.

5. A head phone structure having right and left ear cover speakers, and a head band interconnecting said speakers, the improvement comprising:

a cavity formed in the external surface of one of said ear cover speakers, said cavity containing an external input terminal, and said cavity being dimensioned sufficiently to receive a MP3 player therein, which player is coupled to said input terminal, and keeper means disposed adjacent said cavity for retaining the MP3 player therein, said headphone structure comprising at least one member selected from the group consisting of an anti-noise circuit, a sound collection circuit, and a radio receiving circuit;

said anti-noise circuit comprising a microphone for detecting noise, phased detection U circuits coupled to said microphone and to each speaker and means for emitting a sound wave of opposite phase to said noise, coupled to said speakers;

said radio circuit comprising an AM/FM receiver, a U circuit IC, a down converter circuit, a detect circuit, and a demodulator circuit;

said sound collection circuit comprising an external source audio input terminal, said demodulator circuit and audio input terminal being adapted to be coupled to phase detecting U circuits and to said speakers.

6. The structure of claim 5 wherein said keeper means is a pivotally mounted lever.

7. The structure of claim 5 further comprising a protective cover plate dimensioned to cover said cavity whereby when an MP3 player is mounted therein coupled to said external input terminal, said cover plate will protect said MP3 player.

* * * * *